(12) United States Patent
Yashiro et al.

(10) Patent No.: US 10,261,308 B2
(45) Date of Patent: Apr. 16, 2019

(54) ENDOSCOPE EQUIPPED WITH IMAGE SENSOR AT TIP PORTION

(71) Applicant: FUJIFILM Corporation, Tokyo (JP)

(72) Inventors: Takashi Yashiro, Kanagawa (JP); Shuichi Ishii, Kanagawa (JP); Kazuaki Takahashi, Kanagawa (JP); Ryou Kitano, Kanagawa (JP); Issei Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 226 days.

(21) Appl. No.: 15/249,460

(22) Filed: Aug. 28, 2016

(65) Prior Publication Data
US 2017/0059850 A1 Mar. 2, 2017

(30) Foreign Application Priority Data

Aug. 31, 2015 (JP) .................................. 2015-171442

(51) Int. Cl.
*A61B 1/05* (2006.01)
*G02B 23/24* (2006.01)
(Continued)

(52) U.S. Cl.
CPC ...... *G02B 23/2484* (2013.01); *A61B 1/00096* (2013.01); *A61B 1/05* (2013.01);
(Continued)

(58) Field of Classification Search
CPC ............ G02B 23/2484; G02B 23/2476; H04N 5/2253; H04N 5/2254; A61B 1/05; A61B 1/051; A61B 1/053
See application file for complete search history.

(56) References Cited

U.S. PATENT DOCUMENTS

| 5,305,736 A | 4/1994 | Ito |
| 2011/0102652 A1* | 5/2011 | Lu .................. H04N 5/2253 348/294 |

(Continued)

FOREIGN PATENT DOCUMENTS

| JP | H04338444 | 11/1992 |
| JP | 2008118568 A | * 5/2008 ......... A61B 1/00096 |

(Continued)

OTHER PUBLICATIONS

"Notification of Reasons for Refusal of Japanese Counterpart Application," dated Jun. 26, 2018, with English translation thereof, pp. 1-6.

*Primary Examiner* — John P Leubecker
*Assistant Examiner* — Shankar R Ghimire
(74) *Attorney, Agent, or Firm* — JCIPRNET

(57) ABSTRACT

An endoscope includes, in a tip portion of an insertion unit: an image sensor having a photodetecting surface as defined herein; an imaging optical system as defined herein; a holding frame as defined herein; and a tip portion of a treatment tool channel as defined herein, and, in a cross section taken perpendicularly to the optical axis, a thickness, on a first axis that intersects the optical axis and a center of the treatment tool channel, of frame wall portions, located on two respective sides of the optical axis and intersecting the first axis, of at least a portion of the holding frame is smaller than a thickness, on a second axis that is perpendicular to the optical axis and the first axis, of frame wall portions, located on two respective sides of the optical axis and intersecting the second axis, of the at least portion of the holding frame.

10 Claims, 10 Drawing Sheets

(51) Int. Cl.
*H04N 5/225* (2006.01)
*A61B 1/00* (2006.01)
*A61B 1/07* (2006.01)

(52) U.S. Cl.
CPC .......... *A61B 1/051* (2013.01); *G02B 23/2476* (2013.01); *H04N 5/2253* (2013.01); *A61B 1/07* (2013.01); *H04N 2005/2255* (2013.01)

(56) References Cited

U.S. PATENT DOCUMENTS

| | | | | |
|---|---|---|---|---|
| 2011/0270246 | A1* | 11/2011 | Clark | A61B 18/1492 |
| | | | | 606/41 |
| 2012/0220828 | A1* | 8/2012 | Iwasaki | A61B 1/00188 |
| | | | | 600/109 |
| 2013/0172674 | A1* | 7/2013 | Kennedy, II | A61B 1/018 |
| | | | | 600/109 |
| 2015/0062316 | A1* | 3/2015 | Haraguchi | A61B 1/00009 |
| | | | | 348/65 |
| 2016/0274350 | A1* | 9/2016 | Aizenfeld | G02B 23/2438 |
| 2016/0363757 | A1* | 12/2016 | Imai | G02B 23/2476 |
| 2017/0035279 | A1* | 2/2017 | Fujii | A61B 1/00114 |

FOREIGN PATENT DOCUMENTS

| | | | | |
|---|---|---|---|---|
| JP | 4795202 | B2 * | 10/2011 | ......... A61B 1/00096 |
| JP | 2014230638 | A * | 12/2014 | |
| JP | 2015058118 | | 3/2015 | |
| JP | 2015073537 | | 4/2015 | |
| JP | 2015073537 | A * | 4/2015 | |
| WO | 2015015840 | | 2/2015 | |

* cited by examiner

ENDOSCOPE EQUIPPED WITH IMAGE SENSOR AT TIP PORTION

CROSS-REFERENCE TO RELATED APPLICATIONS

This application claims the benefit of Japanese Patent Application JP 2015-171442, filed Aug. 31, 2015, the entire content of which is hereby incorporated by reference, the same as if set forth at length.

FIELD OF THE INVENTION

The present invention relates to an endoscope which is equipped with an image sensor in a tip portion of an insertion unit to be inserted into a subject body.

BACKGROUND OF THE INVENTION

An image sensor that is installed in a tip portion of an insertion unit of an endoscope and an imaging optical system for forming a subject image on the photodetecting surface of the image sensor are typically disposed in the tip portion of the insertion unit in such a manner as to be housed in a holding frame. The insertion unit of the endoscope is formed with a treatment tool channel in which various treatment tools for treating an observation part can be inserted, and the treatment tool channel and the holding frame which houses the image sensor and the imaging optical system are disposed in the tip portion of the insertion unit adjacent to each other in a radial direction.

JP-A-2015-58118 and JP-A-2015-73537 disclose endoscopes in which a bottom wall, extending alongside a treatment tool channel, of a holding frame that holds an image sensor and an imaging optical system is so thin as to reduce the diameter of the insertion unit having a tip portion in which the holding frame and the treatment tool channel are arranged adjacent to each other in a radial direction.

SUMMARY OF THE INVENTION

In the endoscopes disclosed in JP-A-2015-58118 and JP-A-2015-73537 in which only the bottom wall, opposed to the treatment tool channel, of the holding frame is made thin, an empty space can be formed inside the tip portion of the insertion unit by thinning the entire frame wall of the holding frame. A limited inside capacity of the tip portion can be utilized efficiently by, for example, installing new components in the empty space thus formed.

On the other hand, the strength of the holding frame lowers if the entire frame wall of the holding frame is made thinner. For another thing, where only the bottom wall, opposed to the treatment tool channel, of the holding frame is made thinner as in the endoscopes disclosed in JP-A-2015-58118 and JP-A-2015-73537, the holding frame loses top/bottom symmetry, possibly raising problems such as inclination of the optical axis of the imaging optical system and deviation between the optical axis and the center of the photodetecting surface of the image sensor that are caused by unbalanced deformation of the holding frame.

The present invention has been made in view of the above circumstances, and an object of the invention is therefore to provide an endoscope in which the strength of a holding frame that houses an image sensor and an imaging optical system is kept high and the inside capacity of a tip portion of an insertion unit can be utilized efficiently.

According to an aspect of the invention, there is provided an endoscope comprising, in a tip portion of an insertion unit: an image sensor having a photodetecting surface in a plane that crosses the longitudinal axis of the insertion unit; an imaging optical system which forms a subject image on the photodetecting surface; a holding frame which houses the imaging optical system and the image sensor; and a tip portion, extending parallel with the optical axis of the imaging optical system, of a treatment tool channel, wherein in a cross section taken perpendicularly to the optical axis, the thickness, on a first axis that intersects the optical axis and the center of the treatment tool channel, of frame wall portions, located on two respective sides of the optical axis and intersecting the first axis, of at least a portion of the holding frame is smaller than the thickness, on a second axis that is perpendicular to the optical axis and the first axis, of frame wall portions, located on two respective sides of the optical axis and intersecting the second axis, of the at least portion of the holding frame.

The invention can provide an endoscope in which the strength of a holding frame that houses an image sensor and an imaging optical system is kept high and the inside capacity of a tip portion of an insertion unit can be utilized efficiently.

DESCRIPTION OF SYMBOLS

Figure 1:
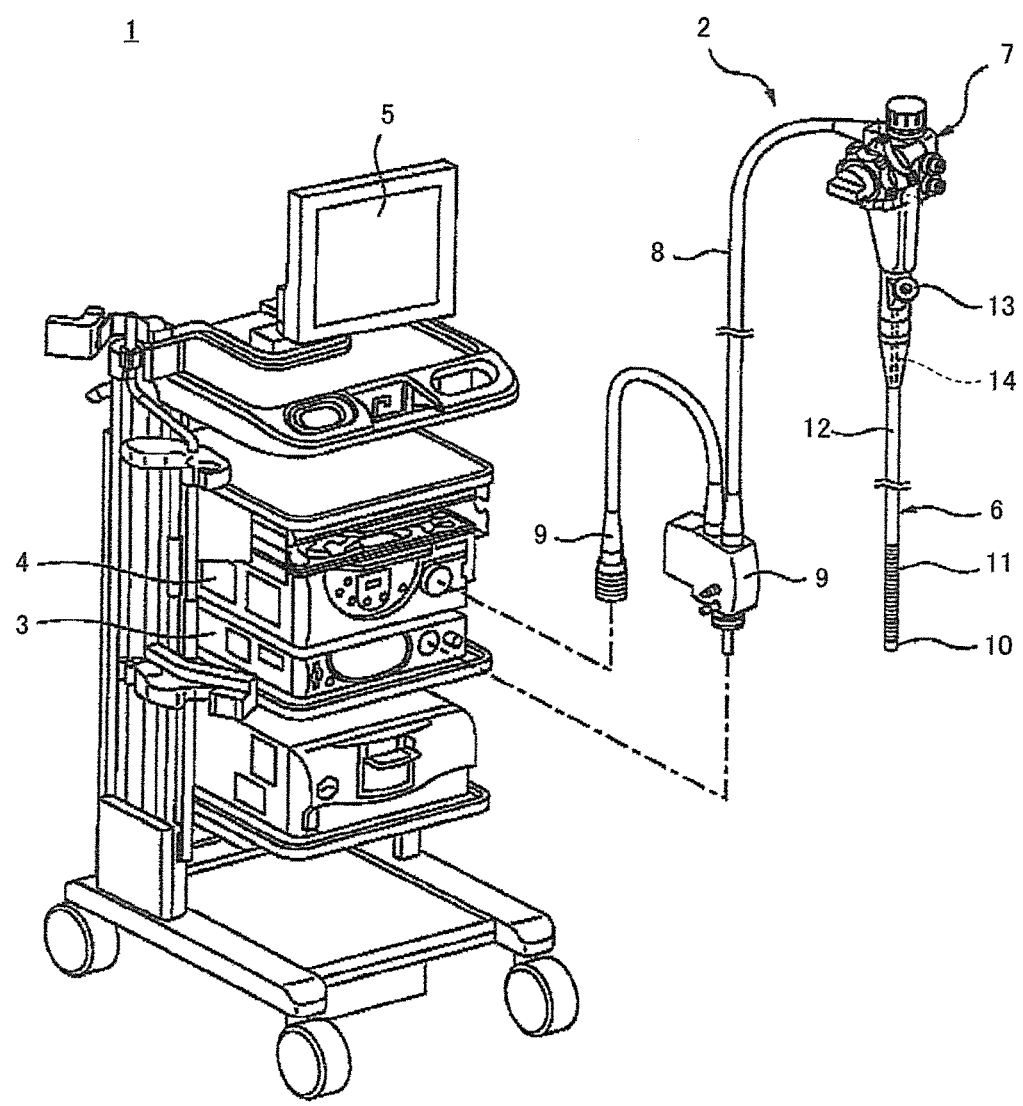
FIG. 1 shows the configuration of an example endoscope system for description of an embodiment of the present invention.

1: Endoscope system
2: Endoscope
3: Light source unit
4: Processor unit
5: Monitor
6: Insertion unit
7: Manipulation unit
8: Universal cord
9: Connectors
10: Tip portion
11: Bendable portion
12: Soft portion
14: Treatment tool channel
20: Image sensor 21: Lens barrel
21a: Imaging optical system
22: Holding frame
29: Cable reinforcement member
30: Sensor holding portion
30a, 30b, 30c, 30d: Frame wall portions
31: Optical system holding portion
31a, 31b, 31c, 31d: Frame wall portions
32: Holding arms
33: Link piece
34c, 34d: Step portions

DETAILED DESCRIPTION OF THE INVENTION

FIG. 1 shows an example endoscope system 1 for description of an embodiment of the present invention. The endoscope system 1 is composed of an endoscope 2, a light source unit 3, and a processor unit 4. The endoscope 2 is equipped with an insertion unit 6 to be inserted into a subject body, a manipulation unit 7 which is continuous with the insertion unit 6, and a universal cord 8 which extends from the manipulation unit 7. The insertion unit 6 is composed of a tip portion 10, a bendable portion 11 which is continuous with the tip portion 10, and a soft portion 12 which links the bendable portion 11 to the manipulation unit 7.

The tip portion 10 is equipped with an illumination optical system for emitting illumination light for illumination of an observation part, an image sensor and an imaging optical system for shooting the observation part, and other components. The bendable portion 11 is configured so as to be bendable perpendicularly to the longitudinal axis of the insertion unit 6, and is bent by manipulating the manipulation unit 7. The soft portion 12 is configured so as to be relatively flexible, that is, flexible enough to deform so as to conform to the shape of an insertion route of the insertion unit 6.

The manipulation unit 7 is equipped with buttons for manipulating an imaging operation of the image sensor installed in the tip portion 10 and a rotary knob for making a manipulation for bending the bendable portion 11. The manipulation unit 7 is formed with an insertion inlet 13 through which a treatment tool such as an electric scalpel is to be inserted, and a treatment tool channel 14 through which a treatment tool is to be inserted is formed in the insertion unit 6 so as to extend from the insertion inlet 13 to the tip portion 10.

Connectors 9 are provided at an intermediate position and one end of the universal cord 8. The endoscope 2 is connected, via the connector(s) 9, to the light source unit 3 for generating illumination light to be emitted from the illumination optical system provided in the tip portion 10 and the processor unit 4 for processing a video signal acquired by the image sensor provided in the tip portion 10. The processor unit 4 generates video data of an observation part by processing a received video signal and displays the generated video data on a monitor 5. Furthermore, the processor unit 4 has the generated video data recorded.

A light guide and cables are disposed inside the insertion unit 6, the manipulation unit 7, and the universal cord 8. Illumination light generated by the light source unit 3 is guided by the light guide to the illumination optical system provided in the tip portion 10, and signals and power are transmitted between the image sensor provided in the tip portion 10 and the processor unit 4 by the cables.

Figure 2:
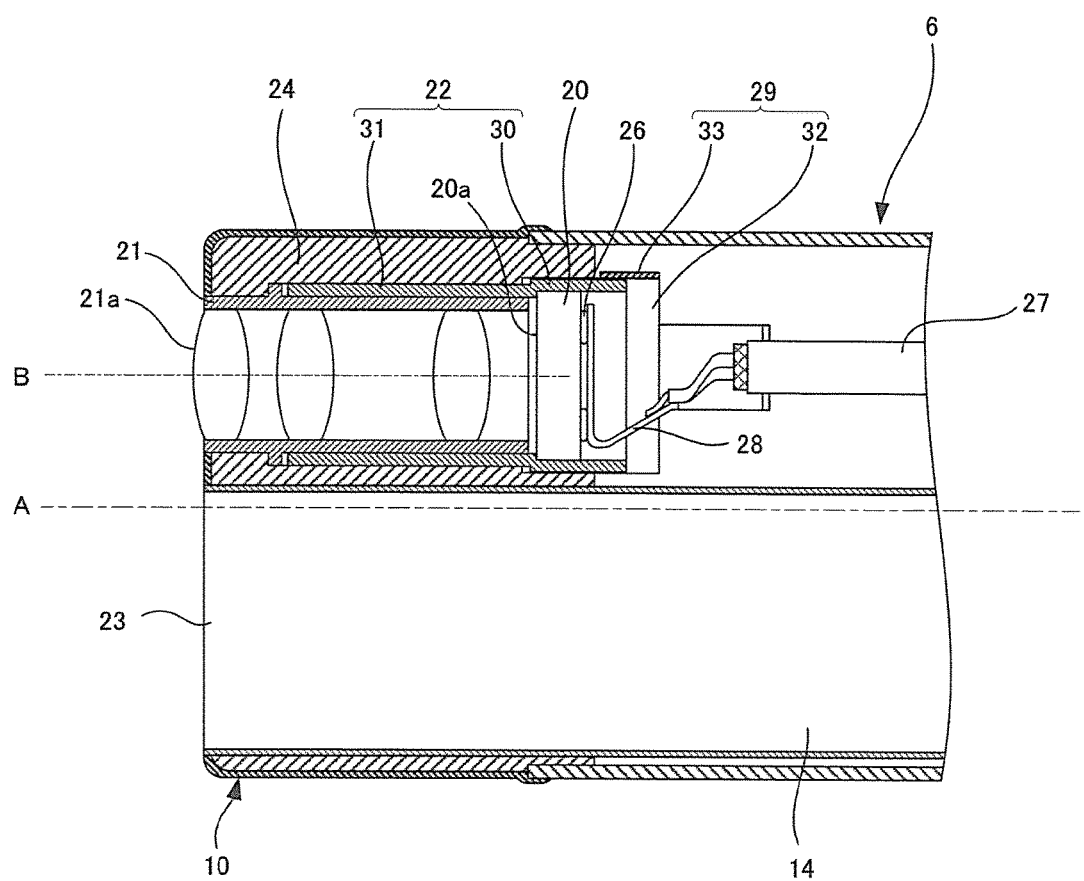
FIG. 2 is a sectional view of a tip portion of an insertion unit of an endoscope shown in FIG. 1.
Figure 3:
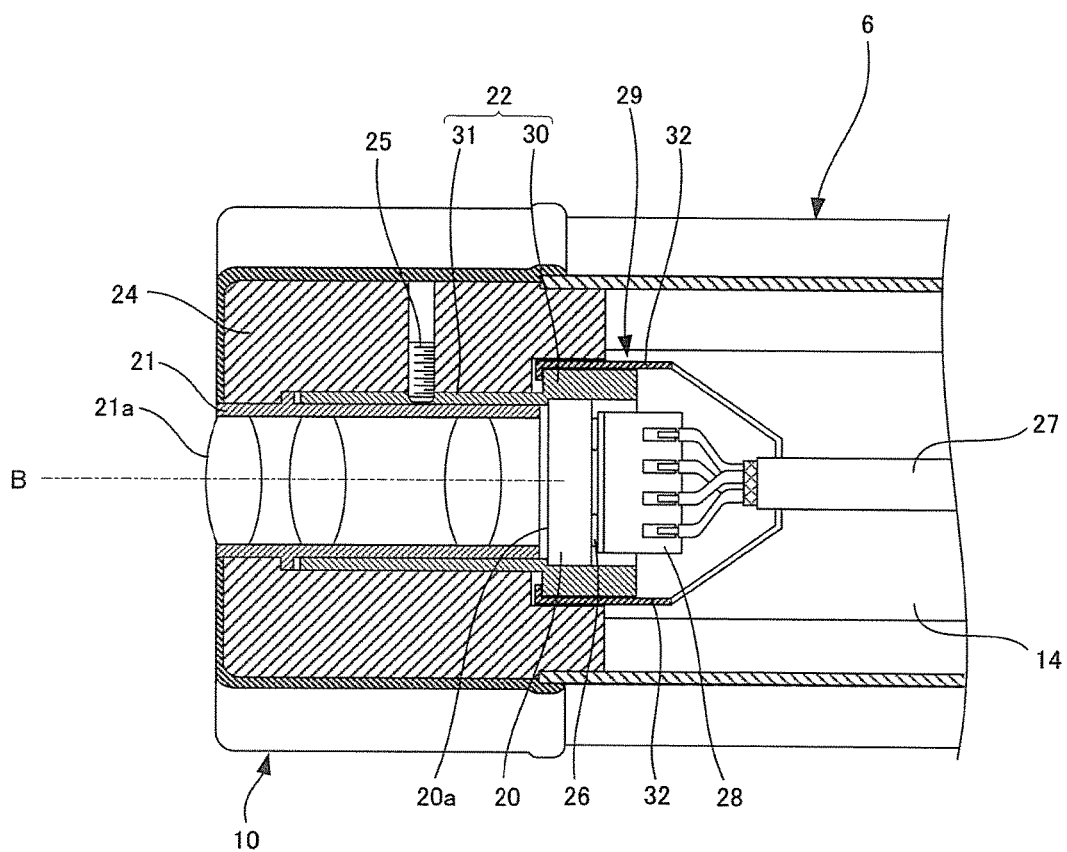
FIG. 3 is another sectional view of the tip portion of the insertion unit of the endoscope shown in FIG. 1.

FIGS. 2 and 3 show the internal configuration of the tip portion 10 of the insertion unit 6. The tip portion 10 is equipped with an image sensor 20 such as a CCD (charge-coupled device) image sensor or a CMOS (complementary metal-oxide-semiconductor) image sensor, a lens barrel 21 which houses an imaging optical system 21a for forming a subject image on a photodetecting surface 20a of the image sensor 20, a holding frame 22 which holds the image sensor 20 and the lens barrel 21, and an outlet 23 of the treatment tool channel 14. Although not shown in FIG. 2 or 3, the illumination optical system for emitting illumination light that is guided from the light source unit 3 by the light guide and other components are disposed in the tip portion 10.

The holding frame 22 has a sensor holding portion 30 which holds the image sensor 20 and an optical system holding portion 31 which holds the lens barrel 21 which houses the imaging optical system 21a. Each of the sensor holding portion 30 and the optical system holding portion 31 is cylindrical, and the image sensor 20 and the lens barrel 21 are housed in and held by the sensor holding portion 30 and the optical system holding portion 31, respectively. The optical system holding portion 31 holds the lens barrel 21 so that it is movable along the optical axis B of the imaging optical system 21a, and the position of the image sensor 20 relative to the imaging optical system 21a can be adjusted by a movement of the lens barrel 21. The lens barrel 21 is fixed to the optical system holding portion 31 with adhesive or the like after positioning of the image sensor 20.

The holding frame 22 is disposed in a housing hole which is formed in a tip hard portion 24 made of a metal material such as stainless steel, and is fixed to the tip hard portion 24. In the illustrated example, the optical system holding portion 31 of the holding frame 22 and the tip hard portion 24 are formed with screw holes that are continuous with each other in a state that the holding frame 22 is set in the housing hole. The holding frame 22 is fixed to the tip hard portion 24 when a screw 25 is threadedly engaged with a screw hole that spans the holding frame 22 and the tip hard portion 24. A tip portion of the treatment tool channel 14 and the illumination optical system are also disposed in respective housing holes formed in the tip hard portion 24, and are fixed to the tip hard portion 24.

The optical axis B of the imaging optical system 21a housed in the lens barrel 21 which is fixed to the tip hard portion 24 is approximately parallel with the longitudinal axis A of the insertion unit 6, and the photodetecting surface 20a of the image sensor 20 on which a subject image is formed by the imaging optical system 21a is oriented approximately perpendicularly to the longitudinal axis A of the insertion unit 6. The tip portion, fixed to the tip hard portion 24, of the treatment tool channel 14 extends parallel with the longitudinal axis A of the insertion unit 6, that is, the optical axis B of the imaging optical system 21a. The holding frame 22 and the treatment tool channel 14 are arranged adjacent to each other in a radial direction of the tip portion of the insertion unit 6.

Plural terminals 26 for input and output of signals and power are formed on the back surface, opposite to the photodetecting surface 20a, of the image sensor 20. The individual conductors of a cable 27 which connects the image sensor 20 to the processor unit 4 (see FIG. 1) are connected to the respective terminals 26 and extend parallel with the longitudinal axis A behind the image sensor 20. Although in the illustrated example the individual conductors of the cable 27 are connected to the terminals 26 via a flexible circuit board 28, they may be connected directly to the terminals 26.

A cable reinforcement member 29 which holds the cable 27 which extends parallel with the longitudinal axis A behind the image sensor 20 is attached to the holding frame 22. The cable reinforcement member 29 has two holding arms 32 and a link piece 33 which links the two holding frame 22.

The two holding arms 32 are disposed so that the sensor holding portion 30 of the holding frame 22 is sandwiched between them. The link piece 33 links the two holding arms 32 by bridging respective edges of the two holding arms 32 which extend parallel with the longitudinal axis A. The two holding arms 32 extend rearward from the holding frame 22 parallel with the longitudinal axis A, and grips, behind the image sensor 20, a terminal portion of the cable 27 which extends parallel with the longitudinal axis A.

The terminal portion of the cable 27 is held between the two holding arms 32, whereby the position of the terminal portion of the cable 27 with respect to the image sensor 20 is fixed. As a result, even if the cable 27 is pushed or pulled as the bendable portion 11 or the soft portion 12, for example, is bent, loads that act on connection portions of the image sensor 20 and the individual conductors of the cable 27 are reduced, whereby the reliability of the connections between the image sensor 20 and the cable 27 is increased.

Figure 4:
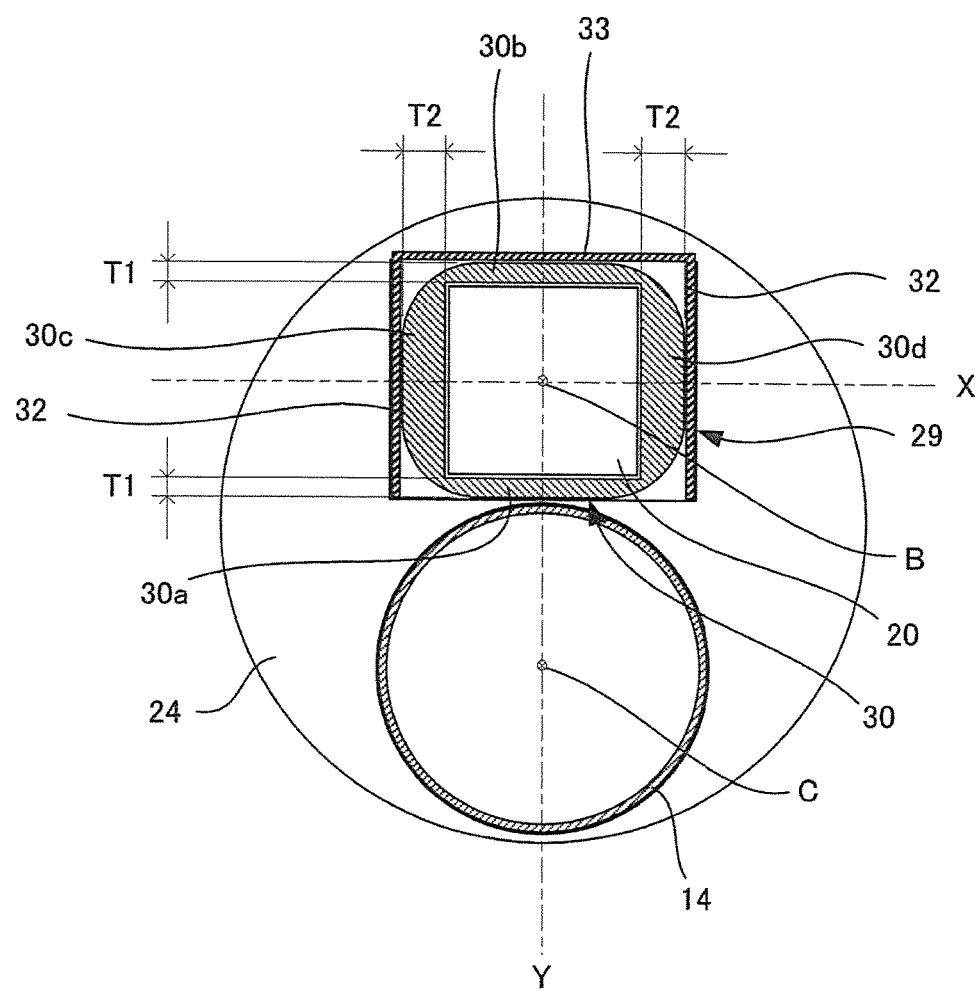
FIG. 4 is a sectional view showing, among other things, a holding frame which houses an image sensor and an imaging optical system of the endoscope shown in FIG. 1.
Figure 5:
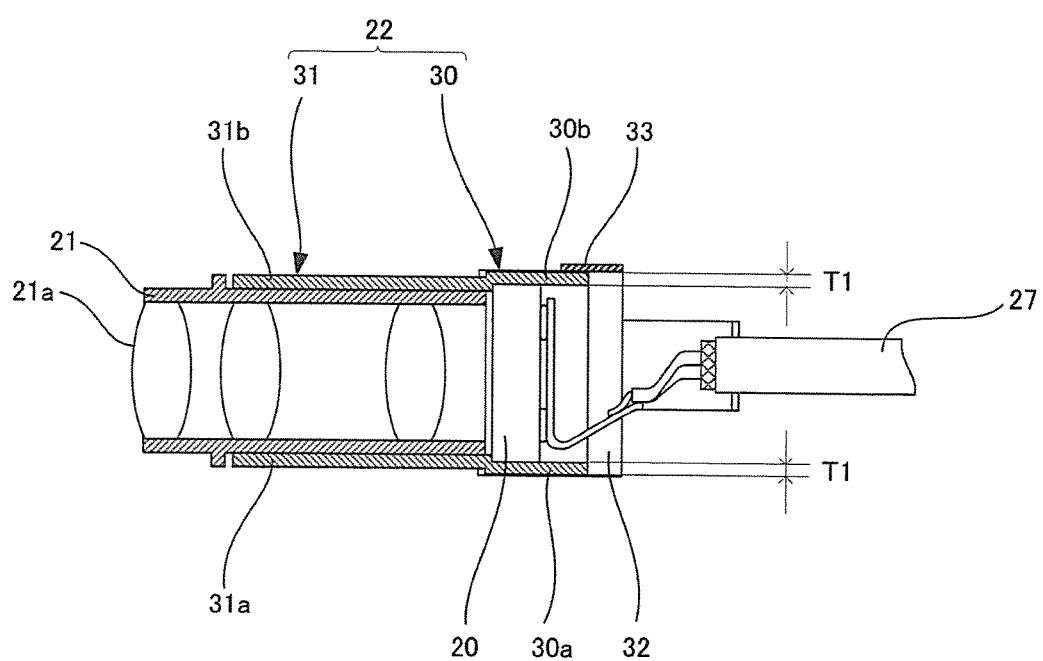
FIG. 5 is another sectional view showing the same holding frame as shown in FIG. 4.
Figure 6:
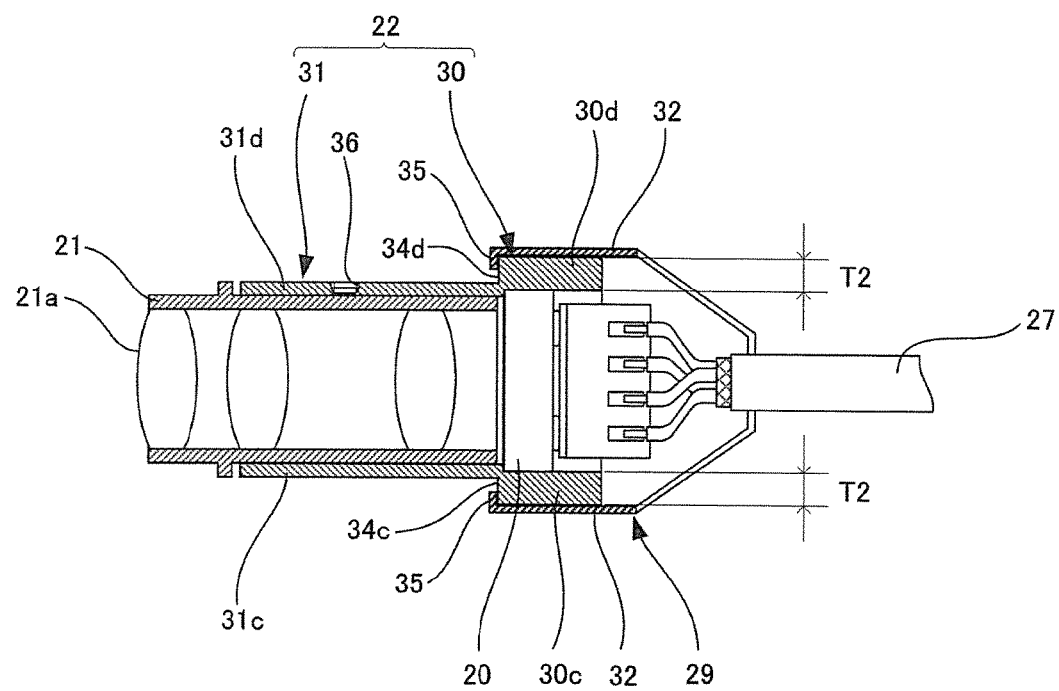
FIG. 6 is a further sectional view showing the same holding frame as shown in FIG. 4.

FIG. 4-6 show the structure of the holding frame 22. In this example, the frame wall of the sensor holding portion 30 of the holding frame 22 is not uniform in thickness.

In a cross section including the sensor holding portion 30 and taken perpendicularly to the optical axis B of the imaging optical system 21a housed in the lens barrel 21, the Y axis is defined as a first axis that intersects the optical axis B of the imaging optical system 21a and the center C of the treatment tool channel 14 and the X axis is defined as a second axis that is perpendicular to the optical axis B and the Y axis. The thickness T1, on the Y axis, of a frame wall portion 30a, adjacent to the treatment tool channel 14, of the sensor holding portion 30 and a frame wall portion 30b, opposite to the frame wall portion 30a, of the sensor holding portion 30 (the frame wall portions 30a and 30b are located on the two respective sides of the optical axis B and intersect the Y axis) is smaller than the thickness T2, on the X axis, of frame wall portions 30c and 30d, located on the two respective sides of the optical axis B and intersecting the X axis, of the sensor holding portion 30.

In the illustrated example, the thickness, on the Y axis, of frame wall portions 31a and 31b, located on the two respective sides of the optical axis B and intersecting the Y axis, of the optical system holding portion 31 and the thickness, on the X axis, of frame wall portions 31c and 31d, located on the two respective sides of the optical axis B and intersecting the X axis, of the optical system holding portion 31 are identical and are equal to the thickness T1 of the frame wall portions 30a and 30b of the sensor holding portion 30. However, as in the sensor holding portion 30, the thickness of the frame wall portions 31a and 31b located on the two respective sides of the optical axis B and intersecting the Y axis may be set smaller than the thickness of the frame wall portions 31c and 31d located on the two respective sides of the optical axis B and intersecting the X axis.

Inside the tip portion of the insertion unit 6, large spaces extending in the X-axis direction exist around the holding frame 22 in contrast to the fact that only small spaces extending in the Y-axis direction exist around the holding frame 22 (the holding frame 22 and the treatment tool channel 14 are adjacent to each other in the Y-axis direction). Therefore, utilizing the above large spaces, the thickness T2 of the frame wall portions 30c and 30d, intersecting the X axis, of the sensor holding portion 30 can be increased without increasing the outer diameter of the insertion unit 6.

By increasing the thickness T2 of the frame wall portions 30c and 30d, the thickness T1 of the frame wall portion 30a which is adjacent to the treatment tool channel 14 and the opposite frame wall portion 30b can be reduced while the holding frame 22 is kept sufficiently strong.

By decreasing the thickness T1 of the frame wall portion 30a which is adjacent to the treatment tool channel 14, the distance between the optical axis B and the center C of the treatment tool channel 14, and hence the diameter of the insertion unit 6, can be reduced.

By decreasing the thickness T1 of the frame wall portion 30b which is opposite to the frame wall portion 30a, the space extending alongside the frame wall portion 30b is expanded. A new component can be installed in the expanded space, which means efficient use of the limited inside capacity of the tip portion of the insertion unit 6.

In this example, the two holding arms 32 of the cable reinforcement member 29 are in contact with the respective frame wall portions 30c and 30d of the sensor holding portion 30 in the X-axis (second axis) direction from outside. And the link piece 33 which links the two holding arms 32 is disposed in the space that extends alongside the frame wall portion 30b.

Furthermore, by setting the thickness T1 of the frame wall portion 30a which is adjacent to the treatment tool channel 14 and the opposite frame wall portion 30b smaller than the thickness T2 of the frame wall portions 30c and 30d, the holding frame 22 can be kept symmetrical with respect to the X axis and the Y axis which intersect the optical axis B, which can suppress such problems as inclination of the optical axis B and deviation between the optical axis B and the center of the photodetecting surface 20a of the image sensor 20.

Although the frame wall portions 30a and 30b may be different from each other in thickness, it is preferable that they have the same thickness, in which case the holding frame 22 can be increased in symmetry with respect to the optical axis B. Likewise, although the frame wall portions 30c and 30d may be different from each other in thickness, it is preferable that they have the same thickness.

In the sensor holding portion 30, the frame wall portions 30c and 30d which are relatively thicker are located outside the frame wall portions 31c and 31d, located on the two respective sides of the optical axis B and intersecting the X axis (second axis) of the optical system holding portion 31. A step portion 34c is formed between the frame wall portion 30c of the sensor holding portion 30 and the frame wall portion 31c of the optical system holding portion 31, and a step portion 34d is formed between the frame wall portion 30d of the sensor holding portion 30 and the frame wall portion 31d of the optical system holding portion 31.

The two holding arms 32, being in contact with the respective frame wall portions 30c and 30d of the sensor holding portion 30 in the X-axis direction from outside, of the sensor holding portion 30 are provided with lock portions 35 which are locked on the step portions 34c and 34d, respectively. The engagement of the lock portions 35 of the two holding arms 32 and the step portions 34c and 34d can increase the strength of the fixing of the cable reinforcement member 29 to the holding frame 22 and can thereby prevent the cable reinforcement member 29 from coming off the holding frame 22 when pulled by the cable 27.

Figure 7:
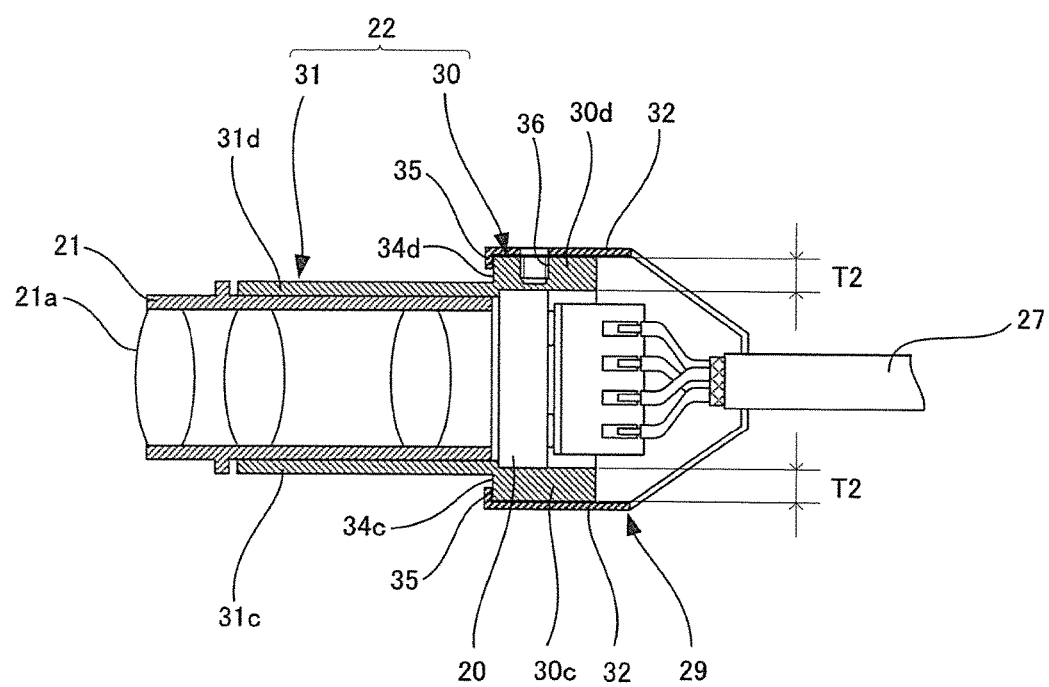
FIG. 7 is a sectional view showing a modification of the holding frame shown in FIG. 4.

FIG. 7 shows a modification of the above-described holding frame 22. In the above-described holding frame 22, as shown in FIG. 6, the screw hole 36 with which the screw 25 is threadedly engaged to fix the holding frame 22 to the tip hard portion 24 is formed through the frame wall portion 31d of the optical system holding portion 31 of the holding frame 22. In contrast, in the holding frame 22 shown in FIG. 7, a screw hole 36 is formed through the sensor holding portion 30, in particular, through the frame wall portion 30d which is thicker than the frame wall portion 31d of the optical system holding portion 31 and the frame wall portions 30a and 30b of the sensor holding portion 30. As a result, the engagement length of the screw 25 and the holding frame 22 can be increased, whereby the fixing of the holding frame 22 to the tip hard portion 24 can be made stronger.

Figure 8:
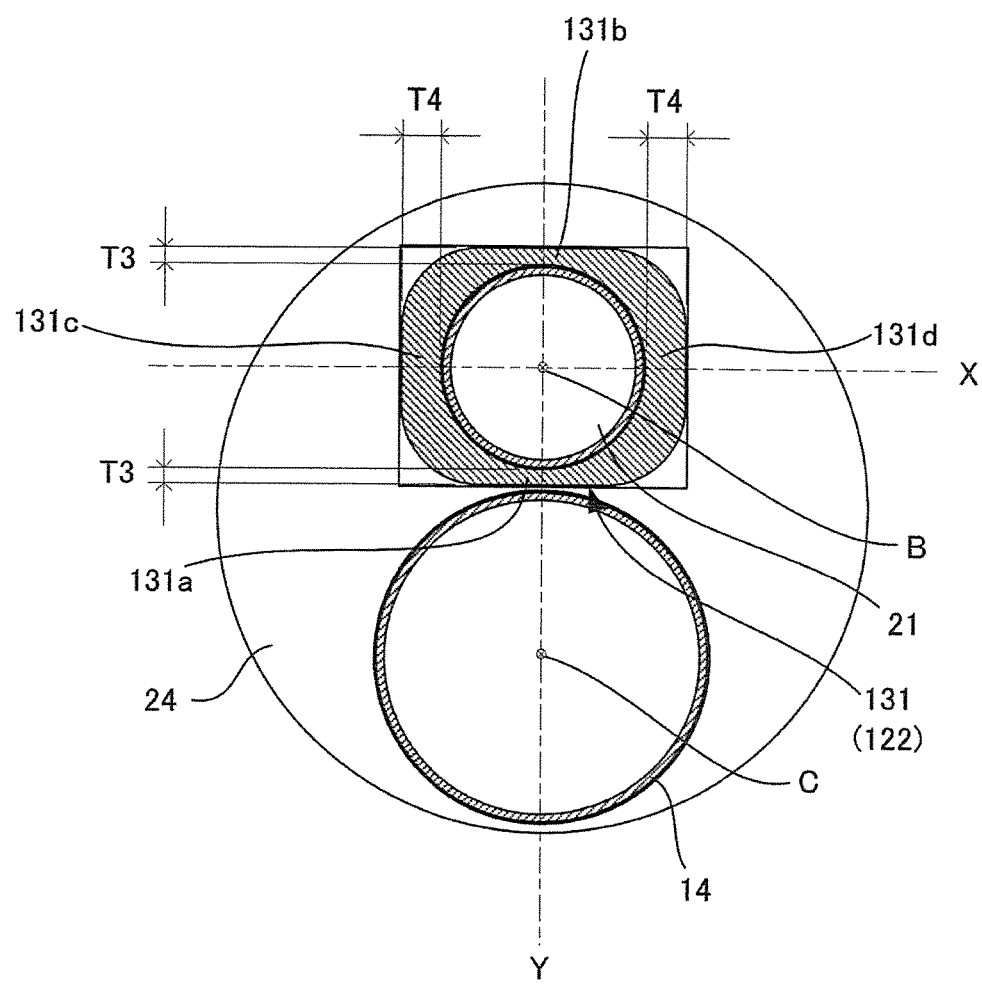
FIG. 8 is a sectional view showing, among other things, another example holding frame which houses the image sensor and the imaging optical system.
Figure 9:
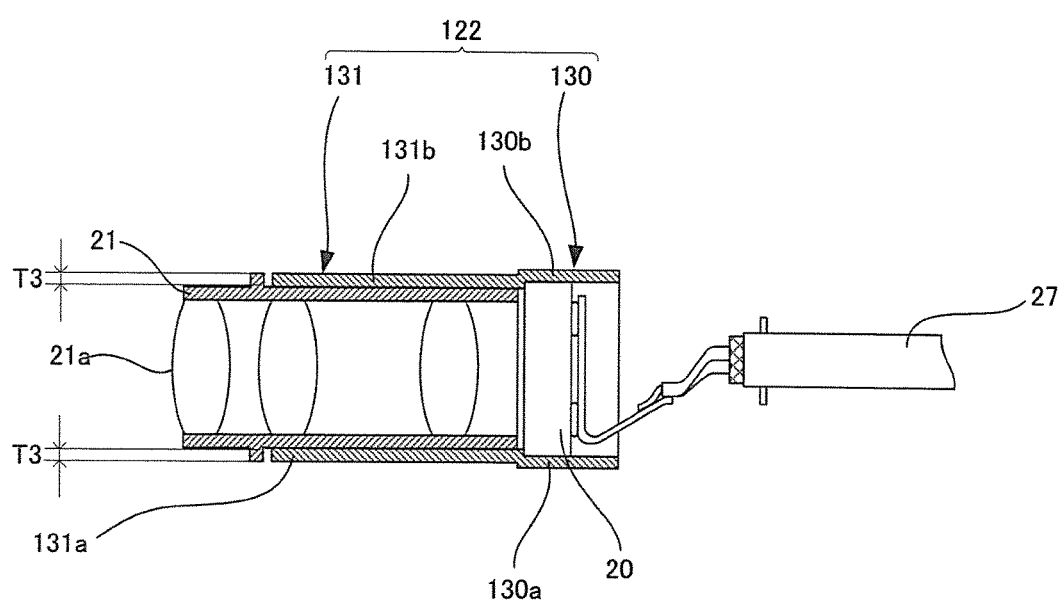
FIG. 9 is another sectional view showing the same holding frame as shown in FIG. 8.
Figure 10:
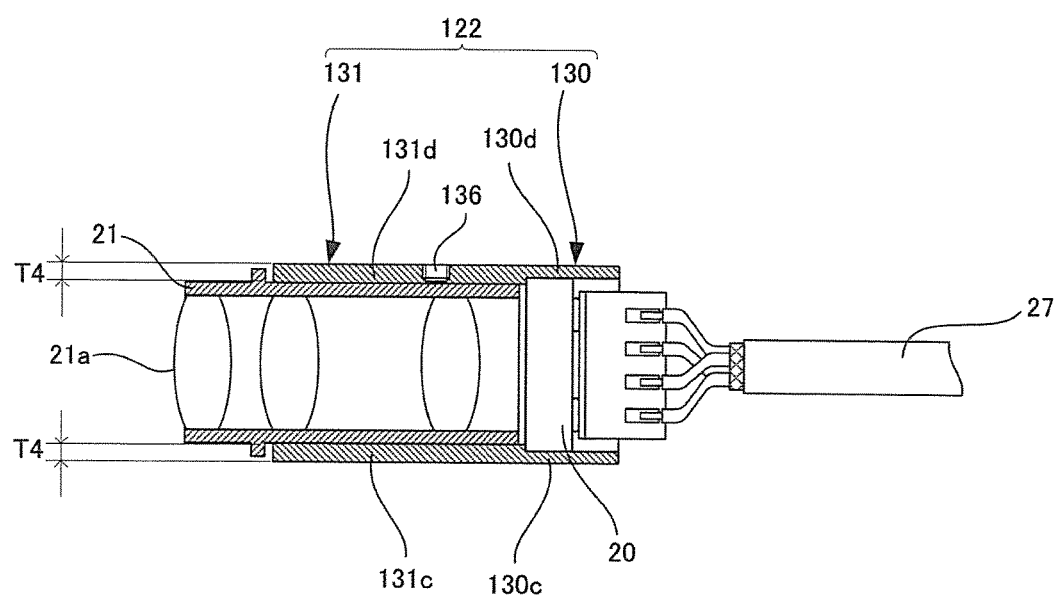
FIG. 10 is a further sectional view showing the same holding frame as shown in FIG. 8.

FIGS. 8-10 show another example holding frame 122 which houses the image sensor 20 and the lens barrel 21. In the example shown in FIGS. 8-10, the frame wall of an optical system holding portion 131 of a holding frame 122 is not uniform in thickness.

In a cross section including the optical system holding portion 131 and taken perpendicularly to the optical axis B of the imaging optical system 21a housed in the lens barrel 21, the Y axis is defined as a first axis that intersects the optical axis B of the imaging optical system 21a and the center C of the treatment tool channel 14 and the X axis is defined as a second axis that is perpendicular to the optical axis B and the Y axis. The thickness T3, on the Y axis, of a frame wall portion 131a, adjacent to the treatment tool channel 14, of the optical system holding portion 131 and a frame wall portion 131b, opposite to the frame wall portion 131a, of the optical system holding portion 131 (the frame wall portions 131a and 131b are located on the two respective sides of the optical axis B and intersect the Y axis) is smaller than the thickness T4, on the X axis, of frame wall portions 131c and 131d, located on the two respective sides of the optical axis B and intersecting the X axis, of the optical system holding portion 131.

In the illustrated example, the thickness, on the Y axis, of frame wall portions 130a and 130b, located on the two respective sides of the optical axis B and intersecting the Y axis, of a sensor holding portion 130 and the thickness, on the X axis, of frame wall portions 130c and 130d, located on the two respective sides of the optical axis B and intersecting the X axis, of the sensor holding portion 130 are identical and are equal to the thickness T3 of the frame wall portions 131a and 131b of the optical system holding portion 131. However, as in the optical system holding portion 131, the thickness of the frame wall portions 130a and 130b located on the two respective sides of the optical axis B and intersecting the Y axis may be set smaller than the thickness of the frame wall portions 130c and 130d located on the two respective sides of the optical axis B and intersecting the X axis.

Inside the tip portion of the insertion unit 6, large spaces extending in the X-axis direction exist around the holding frame 122. Therefore, utilizing the above large spaces, the thickness T4 of the frame wall portions 131c and 131d, intersecting the X axis, of the optical system holding portion 131 can be increased without increasing the outer diameter of the insertion unit 6.

By increasing the thickness T4 of the frame wall portions 131c and 131d, the thickness T3 of the frame wall portion 131a which is adjacent to the treatment tool channel 14 and the opposite frame wall portion 131b can be reduced while the holding frame 122 is kept sufficiently strong.

By decreasing the thickness T3 of the frame wall portion 131a which is adjacent to the treatment tool channel 14, the distance between the optical axis B and the center C of the treatment tool channel 14, and hence the diameter of the insertion unit 6, can be reduced.

By decreasing the thickness T3 of the frame wall portion 131b which is opposite to the frame wall portion 131a, the space extending alongside the frame wall portion 131b is expanded. A new component can be installed in the expanded space, which means efficient use of the limited inside capacity of the tip portion of the insertion unit 6.

Furthermore, by setting the thickness T3 of the frame wall portion 131a which is adjacent to the treatment tool channel 14 and the opposite frame wall portion 131b smaller than the thickness T2 of the frame wall portions 131c and 131d, the holding frame 122 can be kept symmetrical with respect to the X axis and the Y axis which intersect the optical axis B, which can suppress such problems as inclination of the optical axis B and deviation between the optical axis B and the center of the photodetecting surface 20a of the image sensor 20.

Although the frame wall portions 131a and 131b may be different from each other in thickness, it is preferable that they have the same thickness, in which case the holding frame 122 can be increased in symmetry with respect to the optical axis B. Likewise, although the frame wall portions 131c and 131d may be different from each other in thickness, it is preferable that they have the same thickness.

As in the holding frame 22 shown in FIG. 7, a screw hole 136 with which a screw for fixing the holding frame 122 to the tip hard portion 24 is formed through the relatively thicker frame wall portion 131d of the optical system holding portion 131. As a result, the engagement length of the screw 25 and the holding frame 122 can be increased, whereby the fixing of the holding frame 122 to the tip hard portion 24 can be made stronger.

In the above-described insertion units 6 of the endoscopes 2, the imaging optical system 21a is housed in the lens barrel 21 which is separate from the holding frame 22 or 122 and the lens barrel 21 is housed in the holding frame 22 or 122. Alternatively, the lens barrel 21 may be integrated with the holding frame 22 or 122. Also in this case, as in the above-described holding frame 22 or 122, it is possible to set smaller the thickness of a frame wall portion adjacent to the treatment tool channel 14 and an opposite frame wall portion of the holding frame. As a result, the diameter of the insertion unit 6 can be reduced and the limited inside capacity of the tip portion of the insertion unit 6 can be utilized efficiently.

This specification discloses an endoscope comprising, in a tip portion of an insertion unit, an image sensor having a photodetecting surface in a plane that crosses the longitudinal axis of the insertion unit; an imaging optical system which forms a subject image on the photodetecting surface; a holding frame which houses the imaging optical system and the image sensor; and a tip portion, extending parallel with the optical axis of the imaging optical system, of a treatment tool channel, wherein in a cross section taken perpendicularly to the optical axis, the thickness, on a first axis that intersects the optical axis and the center of the treatment tool channel, of frame wall portions, located on two respective sides of the optical axis and intersecting the first axis, of at least a portion of the holding frame is smaller than the thickness, on a second axis that is perpendicular to the optical axis and the first axis, of frame wall portions, located on two respective sides of the optical axis and intersecting the second axis, of the at least portion of the holding frame.

The disclosed endoscope may be such that the holding frame has a sensor holding portion which holds the image sensor; and that the thickness, on the first axis, of frame wall portions, located on two respective sides of the optical axis and intersecting the first axis, of the sensor holding portion is smaller than the thickness, on the second axis, of frame wall portions, located on two respective sides of the optical axis and intersecting the second axis, of the sensor holding portion.

The disclosed endoscope may be such that the holding frame has an optical system holding portion which holds the imaging optical system; and that the frame wall portions, located on the two respective sides of the optical axis and intersecting the second axis, of the sensor holding portion is located outside frame wall portions, located on two respective sides of the optical axis and intersecting the second axis, of the optical system holding portion.

The disclosed endoscope may be such that it further comprises a cable reinforcement member having two holding arms which hold a cable connected to the image sensor; and that the two holding arms are locked on respective step portions that are formed at a boundary between the frame wall portions, intersecting the second axis, of the sensor holding portion and the frame wall portions, intersecting the second axis, of the optical system holding portion.

The disclosed endoscope may be such that the cable reinforcement member has-a link piece which links the two holding arms, and is disposed alongside a frame wall portion that is opposite to a frame wall portion adjacent to the treatment tool channel, of the frame wall portions, located on the two respective sides of the optical axis and intersecting the first axis, of the sensor holding portion.

The disclosed endoscope may be such that the holding frame has an optical system holding portion which holds the imaging optical system; and that the thickness, on the first axis, of frame wall portions, located on two respective sides of the optical axis and intersecting the first axis, of the optical system holding portion is smaller than the thickness, on the second axis, of frame wall portions, located on two respective sides of the optical axis and intersecting the second axis, of the optical system holding portion.

The disclosed endoscope may be such as to further comprise a screw which fixes the holding frame to the tip portion of the insertion unit, and is fixed to a frame wall portion, intersecting the second axis and being relatively thick, of the holding frame.

Although the invention has been described above in relation to preferred embodiments and modifications thereof, it will be understood by those skilled in the art that other variations and modifications can be effected in these preferred embodiments without departing from the scope and spirit of the invention.

What is claimed is:

1. An endoscope comprising, in a tip portion of an insertion unit of the endoscope:
   an image sensor having a photodetecting surface in a plane that crosses a longitudinal axis of the insertion unit;
   an imaging optical system which forms a subject image on the photodetecting surface;
   a holding frame which houses the imaging optical system and the image sensor;
   a cable reinforcement member having two holding arms which hold a cable connected to the image sensor; and
   a tip portion of a treatment tool channel, extending parallel with an optical axis of the imaging optical system,
   wherein in a cross section taken perpendicularly to the optical axis, a first axis intersects the optical axis and a center of the treatment tool channel, a second axis is perpendicular to the optical axis and the first axis, and a thickness of first frame wall portions of the holding frame is smaller than a thickness of second frame wall portions of the holding frame,
   wherein the thickness of the first frame wall portions of the holding frame is in a direction of the first axis, the first frame wall portions of the holding frame are located on two respective sides of the optical axis and intersect the first axis, the thickness of the second frame wall portions of the holding frame is in a direction of the second axis, and the second frame wall portions of the holding frame are located on two respective sides of the optical axis and intersect the second axis,
   wherein the holding frame has a sensor holding portion which holds the image sensor, and the holding arms are disposed on the sensor holding portion.

2. The endoscope according to claim 1, wherein:
   a thickness of first frame wall portions of the sensor holding portion is smaller than a thickness of second frame wall portions of the sensor holding portion,
   wherein the thickness of the first frame wall portions of the sensor holding portion is in the direction of the first axis, the first frame wall portions of the sensor holding portion are located on two respective sides of the optical axis and intersect the first axis, the thickness of the second frame wall portions of the sensor holding portion is in the direction of the second axis, and the second frame wall portions of the sensor holding portion are located on two respective sides of the optical axis and intersect the second axis.

3. The endoscope according to claim 2, wherein:
   the holding frame has an optical system holding portion which holds the imaging optical system; and
   the second frame wall portions of the sensor holding portion are located outside frame wall portions of the optical system holding portion, wherein the frame wall portions of the optical system holding portion are located on two respective sides of the optical axis and intersect the second axis.

4. The endoscope according to claim 3,
   wherein the two holding arms are locked on respective step portions that are formed at a boundary between the second frame wall portions of the sensor holding portion and the frame wall portions of the optical system holding portion.

5. The endoscope according to claim 4, wherein the cable reinforcement member has a link piece which links the two holding arms, and is disposed alongside a first frame wall portion of the first frame wall portions of the sensor holding portion that is opposite to a second frame wall portion of the first frame wall portions of the sensor holding portion adjacent to the treatment tool channel.

6. The endoscope according to claim 5, further comprising a screw which fixes the holding frame to the tip portion of the insertion unit, and is fixed to one of the second frame wall portions of the holding frame.

7. The endoscope according to claim 4, further comprising a screw which fixes the holding frame to the tip portion of the insertion unit, and is fixed to one of the second frame wall portions of the holding frame.

8. The endoscope according to claim 3, further comprising a screw which fixes the holding frame to the tip portion of the insertion unit, and is fixed to at least one of the second frame wall portions of the holding frame.

9. The endoscope according to claim 2, further comprising a screw which fixes the holding frame to the tip portion of the insertion unit, and is fixed to at least one of the second frame wall portions of the holding frame.

10. The endoscope according to claim 1, further comprising a screw which fixes the holding frame to the tip portion of the insertion unit, and is fixed to one of the second frame wall portions of the holding frame.

\* \* \* \* \*